United States Patent [19]

DeVries

[11] Patent Number: 5,072,729
[45] Date of Patent: Dec. 17, 1991

[54] VENTILATOR EXHALATION VALVE

[75] Inventor: Douglas F. DeVries, Redlands, Calif.

[73] Assignee: Bird Products Corporation, Riverside, Calif.

[21] Appl. No.: 441,190

[22] Filed: Nov. 21, 1989

Related U.S. Application Data

[63] Continuation of Ser. No. 927,253, Nov. 4, 1986, abandoned.

[51] Int. Cl.$^5$ .............................................. A61M 16/00
[52] U.S. Cl. .......................... 128/204.23; 128/204.21; 128/205.24
[58] Field of Search ...................... 128/204.21, 204.23, 128/205.24; 251/80, 251, 253

[56] References Cited

U.S. PATENT DOCUMENTS

| | | | |
|---|---|---|---|
| 1,793,226 | 2/1931 | Eggleston et al. | 251/80 |
| 2,503,563 | 4/1950 | Ray . | |
| 2,536,691 | 1/1951 | Miller et al. . | |
| 2,770,231 | 11/1956 | Falk . | |
| 2,770,232 | 11/1956 | Falk | 128/205.18 |
| 2,880,719 | 4/1959 | Andreasen . | |
| 2,904,035 | 9/1959 | Andreasen . | |
| 3,007,490 | 11/1961 | Passmore . | |
| 3,015,963 | 1/1962 | Terry . | |
| 3,306,570 | 2/1967 | Cooksley | 281/251 |
| 3,374,410 | 3/1968 | Cronquist et al. . | |
| 3,416,054 | 12/1968 | Galles . | |
| 3,488,030 | 1/1970 | Hulme et al. . | |
| 3,569,813 | 3/1971 | Clark et al. . | |
| 3,579,279 | 5/1971 | Inaba et al. . | |
| 3,586,953 | 6/1971 | Markhanen et al. . | |
| 3,675,633 | 7/1972 | Nakajima et al. . | |
| 3,813,592 | 5/1974 | Ryberg . | |
| 3,820,539 | 6/1974 | Ollivier . | |

(List continued on next page.)

FOREIGN PATENT DOCUMENTS

| | | |
|---|---|---|
| 8204386 | 6/1982 | PCT Int'l Appl. . |
| 2126666 | 3/1984 | United Kingdom . |

OTHER PUBLICATIONS

Edited by B. C. Kuo, Step Motors and Control Systems, 1979, Chptr 4, entitled "Drive Circuitry for Step Motors", pp. 114–143.

Edited by B. C. Kuo, Step Motors and Control Systems, 1979, Chptr 15, entitled "Microprocessor Control of Step Motors", pp. 391–402.

(List continued on next page.)

Primary Examiner—Randy Citrin Shay
Assistant Examiner—K. Reichle
Attorney, Agent, or Firm—Knobbe, Martens, Olson & Bear

[57] ABSTRACT

A valve in a medical ventilator opens and closes as is needed to permit venting of respiratory gases from a patient to the atmosphere. Changes in position of the valve are caused by a stepper motor, which is joined to the valve by a mechanical linkage. The stepper motor, in turn, is powered by electronic signals from a microcomputer controller. The position of the valve is controlled on a closed loop basis by the controller, which receives feedback regarding the pressure of the proximal gases from a pressure transducer. The valve is uniquely designed to enable the controller to cause the valve to open quickly once the patient begins to exhale, and to permit accurate control over the proximal pressure as the valve is approaching the closed position. In particular, the valve comprises a poppet and a valve seat which have curved mating surfaces, with the curved surface on the poppet being truncated so that pressure gain variance is minimized over the range of positions of the poppet relative to the valve seat. To enhance this improved pressure gain characteristic, a cam in the linkage between the poppet and stepper motor has a variable pitch. All of the components of the valve which are exposed to respiratory gases are easily removed for sterilization and replacement. Further, the poppet is movable to ensure complete closure of the valve despite variability in the tolerances of the replaceable components.

14 Claims, 2 Drawing Sheets

U.S. PATENT DOCUMENTS

| | | |
|---|---|---|
| 3,839,662 | 10/1974 | N'Guyen Van . |
| 3,904,174 | 9/1975 | Giese ................... 281/251 |
| 3,961,627 | 6/1976 | Ernst et al. . |
| 3,968,416 | 7/1976 | Leenhouts . |
| 4,024,447 | 5/1977 | Epstein . |
| 4,027,636 | 6/1977 | Yamamoto et al. . |
| 4,031,448 | 6/1977 | Adachi . |
| 4,036,221 | 7/1977 | Hillsman et al. . |
| 4,081,736 | 3/1978 | Leenhouts et al. . |
| 4,087,732 | 5/1978 | Pritchard . |
| 4,094,285 | 6/1978 | Oyama et al. . |
| 4,107,594 | 8/1978 | Jacobs . |
| 4,119,902 | 10/1978 | Newell . |
| 4,121,578 | 10/1978 | Torzala ............ 128/204.23 |
| 4,126,818 | 11/1978 | Taylor . |
| 4,126,821 | 11/1978 | Gannon . |
| 4,153,021 | 5/1979 | Hattori et al. . |
| 4,158,351 | 6/1979 | Ando et al. . |
| 4,171,697 | 10/1979 | Arion ............... 128/205.24 |
| 4,176,687 | 12/1979 | Ensign . |
| 4,177,830 | 12/1979 | Munson . |
| 4,181,108 | 1/1980 | Bellicardi . |
| 4,199,132 | 6/1980 | deMey, II . |
| 4,204,536 | 5/1980 | Albarda . |
| 4,281,651 | 8/1981 | Cox ................... 128/204.23 |
| 4,285,496 | 8/1981 | Coles . |
| 4,323,064 | 4/1982 | Hoenig et al. . |
| 4,326,513 | 4/1982 | Schulz et al. . |
| 4,333,453 | 6/1982 | Rodder . |
| 4,336,590 | 6/1982 | Jacq et al. . |
| 4,393,869 | 7/1983 | Boyarsky et al. ........ 128/204.21 |
| 4,401,116 | 8/1983 | Fry et al. . |
| 4,421,113 | 12/1983 | Gedeon et al. ........ 128/204.23 |
| 4,448,192 | 5/1984 | Stawitcke et al. . |
| 4,457,339 | 7/1984 | Juan et al. . |
| 4,459,982 | 7/1984 | Fry ............... 128/204.23 |
| 4,484,554 | 11/1984 | Nakajima et al. . |
| 4,527,557 | 7/1985 | DeVries et al. ........ 128/204.23 |
| 4,561,408 | 12/1985 | Jenkins . |
| 4,576,631 | 2/1986 | Durkan ............ 128/204.23 |
| 4,602,653 | 7/1986 | Ruiz-Vela et al. . |
| 4,611,591 | 9/1986 | Inui et al. ........... 128/204.21 |
| 4,635,631 | 1/1987 | Izumi ............. 128/204.23 |
| 4,702,240 | 10/1987 | Chaoui . |

OTHER PUBLICATIONS

Gottlieb, Electric Motors & Control Techniques, 1982, pp. 183–198 and pp. 193–195.

Kenjo, Stepping Motors and their Microprocessor Controls, 1984, pp. 121–165.

Siemens–Elema, "Service Manual", for the Servo Ventilator 900B, 1979, 56 pages.

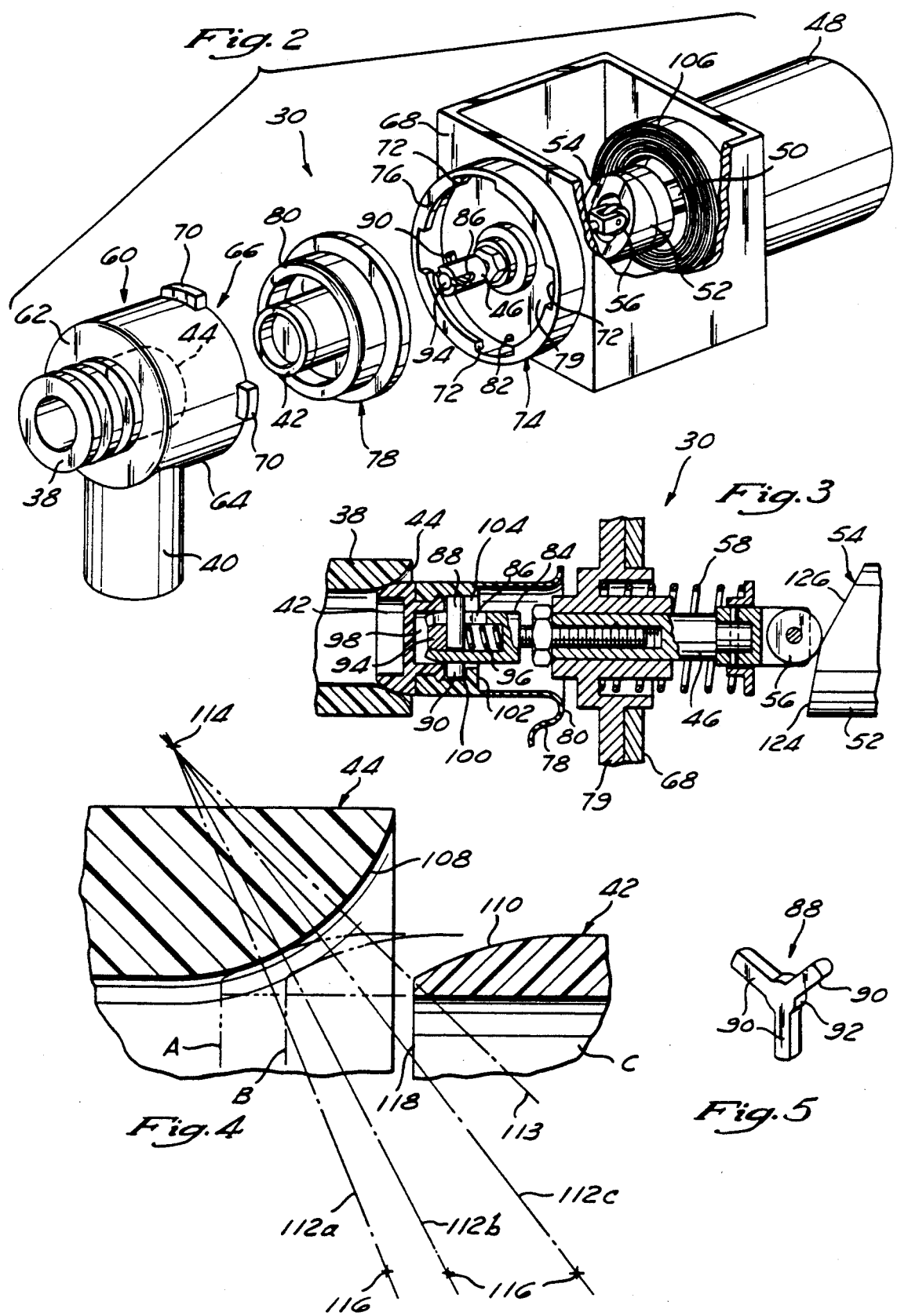

VENTILATOR EXHALATION VALVE

This application is a continuation of application Ser. No. 927,253, filed Nov. 4, 1986, now abandoned.

BACKGROUND OF THE INVENTION

This invention relates generally to the field of medical ventilators, and more particularly to an exhalation valve in a ventilator which, when open, permits the venting of respiratory gases from the patient to the atmosphere.

Medical ventilators have been developed to provide artificial respiration to patients whose breathing ability is impaired. Typically, a ventilator will deliver a breath to the patient from a pressurized source of gas. Flow to the patient during inspiration is governed by a flow control valve. When the flow control valve opens, pressurized gas is introduced to the patient's lungs. After the flow control valve closes, ending the inspiration phase of the breath, the patient's respiratory gases are vented to the atmosphere through an exhalation valve, which opens after inspiration is completed and closes before the next inspiration phase begins.

Previous ventilators have been capable of operating in several modes so that the degree of support that the ventilator provides to the patient's natural breathing patterns can be varied. At one extreme, the ventilator can provide fully controlled ventilation in which the ventilator has complete control over when the breath is delivered and the volume of gases received by the patient during each breath. In the fully controlled mode, all of the flow parameters are preset by an operator in accordance with the particular needs of the patient.

At the other extreme, the ventilator can be programmed to permit "spontaneous" breathing by the patient. During the spontaneous breathing mode, the breath rate, the volume of gas inhaled during each breath, and other flow parameters are not predetermined. The inspiration and expiration phases of each breath are commenced in response to efforts by the patient. In between the "volume controlled" and the "spontaneous breath" modes, various degrees of ventilator-supported respiration are available.

One of the parameters which can be controlled by the ventilator during all modes of ventilation is the pressure within the patient's lungs after the expiration is complete. Therapists have found that in some patients, it is beneficial to maintain a slight positive pressure within the lungs after expiration, so as to avoid the possibility of lung collapse. The pressure of the gases in or near the patient's lungs and airway is called the "proximal pressure". Previous ventilators have included a "positive end expiration pressure" (PEEP) feature, which enables the operator to predetermine what the minimum proximal pressure will be after each expiration phase is completed.

To achieve this end, previous ventilators have included microcomputer controllers which "servo" the position of the exhalation valve to maintain the desired proximal pressure level at the end of each breath. In other words, the controller positions the valve based on feedback from a pressure sensor, and causes movement of the valve as is needed to maintain the proximal pressure at the predetermined level.

A difficulty in the design of exhalation valves is that in order to maintain accurate control over the pressure as the valve closes to end the exhalation flow, small amounts of displacement of the valve should not result in large pressure changes. However, the opposite is true when the valve is initially opened at the beginning of exhalation when flow is greater; then it is desirable to have the valve open quickly. This enables a small pressure drop through the valve, thus providing an unobstructed passageway which closely approximates normal breathing, where there is no resistance to exhalation.

One effort to solve this design problem is disclosed in U.S. Pat. No. 4,527,557, in which an exhalation valve is shown which is driven by a combination of electromechanical and pneumatic components. As a result, the valve is complex and expensive to manufacture. Further, due to the lag time associated with pneumatic systems, the valve sacrifices a quick opening capability for the ability to accurately control pressure.

Thus, a need exists for a ventilator having an inexpensive exhalation valve which performs well when the valve needs to open quickly, as well as when the valve is approaching the closed position and is maintaining a predetermined pressure level.

SUMMARY OF THE INVENTION

The present invention comprises a ventilator having an exhalation valve which, when open, allows venting of proximal gases to the atmosphere. The valve is driven directly by a stepper motor which has a movable shaft. Mechanical means are provided so that movement of the shaft directly causes movement of the valve. The valve position is controlled by a control means which sends electrical signals to the stepper motor.

In one embodiment, the ventilator includes a pressure transducer which measures the pressure of the proximal gases and inputs a signal indicative of the proximal pressure to the control means. The control means compares the input from the pressure transducer with a predetermined pressure level and causes opening and closing of the exhalation valve as is necessary to maintain the proximal pressure equal to the predetermined pressure.

Uniquely, a direct mechanical link is established between the stepper motor and the valve itself. As a result, the lag time between the sending of a signal from the control means to the valve and an actual change in proximal pressure is minimal. Thus, the valve can be opened quickly to eliminate any resistance to exhalation. The stepper motor also permits small, incremental adjustments in the position of the valve so that the pressure level of the proximal gases can be accurately controlled as the valve closes at the end of each breath. Additionally, since no pneumatic components are utilized in causing the valve position to change, the valve is simple in construction and highly reliable.

Preferably, the present valve also comprises a valve member which is movable relative to a valve seat to vary the flow rate through the valve. The valve member includes a convexly curved surface which engages a convexly curved surface on the valve seat when the valve is fully closed. These mating curved surfaces interact so that as the valve member approaches the closed position, the pressure gain of the proximal gases, i.e., the rate of change of pressure relative to displacement of the valve member, is relatively small. Advantageously, this aids in the control of the proximal pressure as the valve closes. Additionally, the curved surface of the valve seat is truncated so that once the valve is opened beyond a certain point, the pressure gain is relatively high. As a result, the valve can be quickly opened to a position at which there is very low resistance to the discharge of respiratory gases to the atmosphere.

Another feature which aids in controlling proximal pressure while still allowing quick opening of the valve is the design of a rotatable cam. The cam is part of the mechanical linkage between the stepper motor and the valve member. In particular, the cam has a cam surface which has two distinct portions with different pitches. The result is that as the valve approaches the closed position, the first portion of the cam governs movement of the valve member. The pitch of the first portion of the cam is small so that for a given amount of cam rotation, a small displacement of the valve member results. When the valve has been opened partially, the second portion of the cam surface governs movement of the valve. The second portion has a steeper pitch so that for a given amount of cam rotation a large displacement of the valve member results.

Another aspect of the invention is that all of the components of the valve which are "wetted", or exposed to respiratory gases, are easily removable for sterilization or replacement. The valve member is removably mounted on a stem, which moves to cause displacement of the valve member relative to the valve seat. A removable cap has an inlet in fluid communication with the patient, and an outlet which allows venting of the respiratory gases to the atmosphere. A diaphragm surrounds the valve member and forms a seal therewith so that the stem and a means for causing displacement of the stem are sealed from contact with the respiratory gases. The diaphragm is also removable, and is flexible to compensate for displacement of the valve member.

A switch is provided on the valve so that upon removal of the cap, the ventilator automatically shuts down. This beneficially prevents the ventilator from attempting to deliver artificial respiration when the ventilator has been disconnected from the patient.

To aid in the seating of the valve member on the valve seat despite dimensional variations between removable parts which are interchangeable, the valve member is secured to a movable member on the valve stem. In the event that dimensional variations cause the valve stem to overshoot the position at which the valve actually is closed, the valve member remains stationary relative to the valve seat as the movable member moves from a first position to a second position. This avoids damage to either the valve member or the valve seat as the stem overshoots. The movable member is biased to the first position, or in the direction towards the valve seat, to ensure proper seating of the valve member on the valve seat and full closure of the valve despite dimensional variations between the interchangeable parts which would otherwise cause separation between the valve member and valve seat.

Another feature of the invention is that the shaft of the stepper motor which drives the valve is biased by a spring so that in the event of a malfunction, the valve is automatically opened. This prevents respiratory gases from being trapped in the patient's lung in the event of a power loss which would otherwise leave the valve in a closed position indefinitely.

BRIEF DESCRIPTION OF THE DRAWINGS

FIG. 2 is an exploded perspective view of an exhalation valve according to the present invention.

FIG. 3 is an assembly view, taken in cross section, of the exhalation valve shown in FIG. 2.

FIG. 4 is an enlarged, cross-sectional view of a valve seat and a valve member according to the present invention, with the valve member shown approaching the closed position in broken lines.

FIG. 5 is a perspective view of a movable starshaped member on which the valve member is mounted.

DETAILED DESCRIPTION OF A PREFERRED EMBODIMENT

Figure 1:
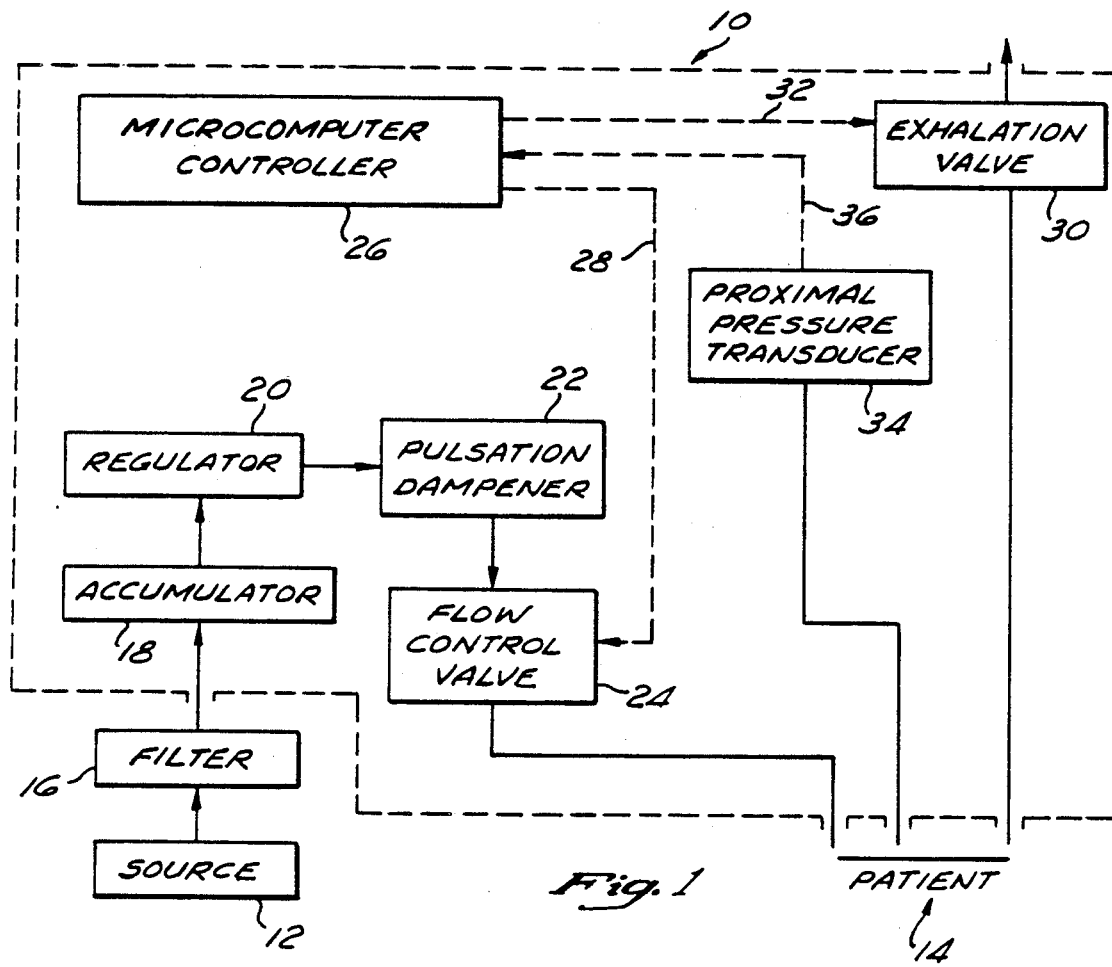
FIG. 1 is a schematic view of the pneumatic layout of the ventilator according to one embodiment of the present invention.

Referring to FIG. 1, the present ventilator is shown generally at 10. The ventilator 10 receives pressurized gas, such as air or an oxygen blend, from a source 12 and controls the flow of gas to a patient 14 so as to provide artificial respiration. As will be apparent to those skilled in the art, the schematic of FIG. 1 has been simplified by the elimination of various commonly used elements such as check valves, safety valves, pressure gauges, etc.

A description of the components illustrated in FIG. 1, and their operation, will be understood from the following description of the flow path of gas through the ventilator 10. The gas initially passes from the source 12 through a coalescing filter 16, so as to remove both liquids and solids from the gas stream. After being filtered, the gas enters an accumulator 18 which is a rigid chamber for the temporary storage of the pressurized gas. The accumulator 18 acts as a reservoir from which gas is drawn during periods of peak demand, such as during inspiration by the patient 14. Downstream of the accumulator 18, a pneumatic regulator 20 is positioned. Gas flowing from the regulator 20 is maintained at a constant pressure of approximately 20 psig, which is referred to herein as the "system pressure."

System pressure gas enters a pulsation dampener 22 which, like the accumulator 18 is a rigid gas storage chamber. However, the volume of the pulsation dampener 22 is smaller than that of the accumulator 18, and the gas in the pulsation dampener 22 is at the system pressure. The pulsation dampener 22 serves to damp out pressure changes caused by transient flow conditions so as to maintain pressure downstream of the regulator 20 at a constant 20 psig.

The pulsation dampener 22 feeds gas to a flow control valve 24. The flow control valve 24 regulates the flow rate of gas which is delivered to the patient 14 during inspiration. The flow control valve 24 can assume a plurality of positions, so as to permit various flow rates of gas to the patient 14. The position of the flow control valve 24 is controlled by a microcomputer controller 26. An electronic signal 28 is sent by the controller 26 to cause opening or closing of the valve 24.

Although not shown, the patient 14 is fitted with an endotracheal tube which establishes fluid communication between the patient's lungs and the ventilator 10. As is well known, the endotracheal tube is inserted in the patient's trachea or wind pipe, and is surrounded by a balloon which forms a seal with the trachea so that all gas flow into and out of the lungs takes places through the endotracheal tube, which is in fluid communication with the ventilator 10.

An exhalation valve 30 is provided to establish fluid communication between the patient's lungs and the atmosphere. When open, the exhalation valve 30 permits the patient 14 to exhale by venting respiratory gases to the atmosphere through the endotracheal tube. Opening and closing of the exhalation valve 30 is governed by the controller 26, which sends an electronic signal 32 to the exhalation valve 30 to effect a change in the position of the exhalation valve 30. The controller 26 determines the proper position of the exhalation valve 30 based on feedback from a proximal pressure transducer 34. The proximal pressure transducer 34 measures the pressure of the gas on the ventilator side of the seal formed by the endotracheal tube, which is referred to as the "proximal" gas. Feedback to the controller 26 is in the form of an input signal 36 from the proximal pressure transducer 34, which is an electrical analog of the proximal pressure.

When the ventilator 10 is operating in a fully controlled mode, in which the patient 14 has no control over the flow parameters, inspiration begins when the flow control valve 24 is signalled to open by the controller 26. Opening of the flow control valve 24 causes gas to enter the patient's lungs through the endotracheal tube. The exhalation valve 30 remains closed during inspiration so that the gas in the endotracheal tube does not leak to the atmosphere. When the flow control valve 24 closes on command from the controller 26, the inspiration phase of the breath terminates.

The expiration phase is commenced by the opening of the exhalation valve 30, the timing of which is determined by the controller 26. Upon opening of the exhalation valve 30, gas within the patient's lungs is automatically expelled to the atmosphere. The exhalation valve 30 closes after the patient 14 has finished exhaling. The ventilator 10 includes a positive end expiration pressure (PEEP) feature so that an operator can preset what the pressure level of the proximal gases should be at the end of each breath. During expiration, the controller 26 compares the actual proximal pressure to the predetermined pressure level (PEEP) and when the proximal pressure reaches the predetermined level, the controller 26 sends a signal 32 to cause the valve 30 to approach the closed position. The controller 26 then "servos", or controls the position of the valve 30 on a closed loop basis so as to maintain the actual proximal pressure equal to the predetermined pressure. After the exhalation valve 30 is completely closed, the flow control valve 24 opens to end the expiration phase and begin the inspiration phase again. This cycle is repeated continuously to establish artificial respiration.

Turning now to FIGS. 2 and 3, the exhalation valve 30 is shown in greater detail. Flow from the patient 14 enters the exhalation valve 30 through a tubular inlet 38, and is vented to the atmosphere through a tubular outlet 40. The position of the valve 30 is changed by movement of a valve member or poppet 42 relative to a valve seat 44. The valve seat 44 is annular in shape and is formed on the end of the inlet tube 38. The poppet 42 is a circular disk which is sized so that the periphery of the poppet 42 sealingly engages the valve seat 44 so as to close off all flow through the valve 30. Displacement of the poppet 42 relative to the valve seat 44 varies the orifice area of the inlet 38 through which gas flow is permitted, thus varying the flow rate through the valve 30 and the pressure of the gases in the inlet tube 38.

The poppet 42 is secured to one end of an elongate stem 46 which is slidable in a linear fashion, substantially parallel to a longitudinal axis of the stem 46. Movement of the stem 46 results in displacement of the poppet 42 relative to the valve seat 44. The stem 46 is driven by a stepper motor 48 which has a rotatable shaft 50. A cam 52 having an axially facing cam surface 54 is secured to one end of the shaft 50. A cam follower or roller 56 is biased into engagement with the cam surface 54 by means of a coil spring 58 surrounding the stem 46. The cam follower 56 is secured to one end of the stem 46 so that rotation of the shaft 50 and the cam 52 causes movement of the stem 46, and ultimately, displacement of the poppet 42.

All of the components of the exhalation valve 30 which are exposed to respiratory gases are removable so that they may be sterilized or replaced by interchangeable, sterile components. In particular, the inlet 38 and outlet 40 are formed as part of a removable cap 60. The cap 60 is hollow and cylindrical in shape. The inlet 38 extends axially through a closed end 62 of the cap 60, and the outlet 40 extends radially outwardly from a side wall 64 of the cap 60. The cap 60 has an open end 66 which engages a valve housing 68 when the valve 30 is fully assembled. The housing 68 surrounds the components of the valve 30 which are not exposed to respiratory gases. To removably secure the cap 60 to the housing 68, lugs 70 are spaced about the periphery of the open end 66 of the cap 60. The lugs 70 mate with notches 72 in an annular retainer member 74 mounted on the housing 68. After passing the lugs 70 through the notches 72, rotation of the cap 60 secures the cap 60 to the housing 68 by engaging the lugs 70 with a radially inwardly extending lip 76 on the retainer 74.

The stem 46 extends through the housing 68 and is protected from respiratory gases by means of a flexible, annular diaphragm 78. The outer periphery of the diaphragm 78 is circular and fits within the retainer member 74. When the cap 60 is secured to the housing 68, the diaphragm 78 is sandwiched between the open end 66 of the cap 60 and a planar vertically oriented surface 79 on the retainer 74 which is flush with the housing 68. The diaphragm 78 thus forms a seal between the cap 60 and the surface 79. The poppet 42 is surrounded by and fixed to the diaphragm 78 so that a seal is formed between the poppet 42 and the surface 79, fully protecting the stem 46 and components within the housing 68 from gas flow through the cap 60. The poppet 42 is removably secured to the stem 46 so that the poppet 42 and diaphragm 78 can be removed as a unit for sterilization. Several concentric folds or convolutions 80 in the diaphragm 78 permit the diaphragm 78 to flex and compensate for movement of the poppet 42 and stem 46 as the valve 30 changes positions.

When secured to the housing 68, the cap 60 depresses a switch 82 on the housing 68, which indicates to the controller 26 that the valve 30 is assembled and operational. Upon removing the cap 60, the switch 82 changes positions and indicates to the controller 26 that the ventilator 10 should be automatically shut down. If the operator accidentally leaves the ventilator 10 turned on while removing the cap 60, this feature prevents the ventilator 10 from unsuccessfully attempting to deliver artificial respiration without a patient being connected to the ventilator 10.

As shown in FIGS. 2 and 3, the poppet 42 is mounted on a tubular portion 84 of the stem 46 which has three equally spaced, parallel, axially oriented slots 86 which start at the end of the stem 46 and extend inwardly. Within the tubular portion 84 of the stem 46, a star shaped member 88 is positioned. As is best seen in FIG. 5, the star 88 has three equally spaced legs 90 radiating outwardly from a central portion 92. The legs 90 protrude through the slots 86 in the stem 46, and the central portion 92 of the star 88 is slidable within the tubular portion 84 of the stem 46. To retain the star 88 inside the tubular portion 84, a plug 94 is pinched within the open end of the tubular portion 84. A coil spring 96 is positioned within the tubular portion 84 and biases the star 88 toward the plug 94, or toward the end of the stem 46 on which the poppet 42 is removably mounted.

One end of the poppet 42 engages the valve seat 44, while the other end of the poppet 42 is designed to mate with the star 88 so that the poppet 42 can be removably secured to the stem 46. As shown in FIG. 3, the poppet 42 includes a central bore 98 through which the end of the tubular portion 46 is inserted. Three arcuate slots 100, each corresponding to a leg 90 of the star 88, surround the central bore 98. The slots 100 are enclosed by a radially inwardly extending lip 102. Notches 104 in the lip 102 permit the legs 90 to be inserted into the arcuate slots 100, after which twisting of the poppet 42 relative to the star 88 engages the legs 90 with the lip 102 so that the poppet 42 is securely attached to the stem 46.

As the star 88 slides relative to the stem 46, the poppet will move also. The spring 96 causes the star 88 and poppet 42 to be biased to the left, or toward the valve seat 44. The central bore 98 is deep enough so that a space is provided into which the end of the tubular portion 84 can slide upon movement of the star 88 and poppet 42 to the right, or away from the valve seat 44.

An optical sensor (not shown) is mounted on the shaft 50 to provide feedback to the controller 26 as to when the shaft 50 has rotated to a position which causes the valve 30 to be fully closed. No other feedback is provided to the controller 26 as to whether the valve 30 actually is closed. Biasing of the poppet 42 relative to the stem 46 ensures that the poppet 42 will fully seat on the valve seat 44 and close the valve 30 when the optical sensor indicates closure.

Since the valve seat 44 is formed as a part of the removable cap 60, and since the poppet 42 itself is removable, compensation must be made for dimensional variations if the cap 60 and poppet 42 are to be interchangeable with replacement parts. Otherwise, extremely precise tolerances would be required to insure that the poppet 42 will always engage the valve seat 44 at the precise point of rotation of the shaft 50 which corresponds to the indication of closure by the optical sensor.

The spring 96 normally biases the poppet 42 far enough toward the closed position so that, even in the case of the largest dimensional variations that cause the poppet 42 to be separated from the seat 44, the poppet 42 will sealingly engage the seat 44. Thus, the stem 46 cannot "undershoot" the actual closed position of the valve 30 when the optical sensor reads that the valve 30 is closed.

Likewise, if the parts are dimensioned so that the valve 30 is closed before the optical sensor indicates closure, "overshooting" of the stem 46 is compensated for by movement of the star 88 and poppet 42 to the right relative to the stem 46, so as to compress the spring 96. Thus, the stem 46 will continue to move as the poppet 42 and valve seat 44 remain stationary relative to each other. As a result, damage to either the valve seat 44 or the poppet 42 is prevented in the case of stem overshoot.

As illustrated in FIG. 2, a spirally-wound spring 106 formed from a thin, metallic strip surrounds the stepper motor shaft 50. The spring 106 biases the shaft 50 to rotate in a direction which causes the valve 30 to open. During normal operation, the stepper motor 48 overcomes the biasing torque generated by the spring 106 so that the spring 106 does not affect the position of the valve 30. However, in the event of a power loss, the spring 106 automatically biases the valve 30 to an open position. This allows the patient 14 to exhale to the atmosphere in the event of such an emergency.

FIG. 4 illustrates the engagement between the mating surfaces of the poppet 42 and the valve seat 44. The valve seat 44 includes a convexly curved surface 108 which faces radially inwardly and forms the internal periphery of the valve seat 44. A convexly curved surface 110 also forms the external periphery of the poppet 42. When the valve 30 is in the closed position, the curved surface 110 of the poppet 42 sealingly engages the curved surface 108 of the valve seat 44, as illustrated when the poppet 42 is in position A, shown in broken lines.

As the poppet 42 is displaced away from the valve seat 44 along a linear axis of motion, causing opening of the valve 30, an annular orifice for gas flow is formed between the poppet 42 and the valve seat 44. When the valve 30 opens initially, the cross-sectional area of the orifice is smallest along a line 112a drawn from a center of curvature 114 of the valve seat curved surface 108 to a center of curvature 116 of the poppet curved surface 110.

As the poppet 42 is displaced between position A to a position B, also shown in broken lines, the change in orifice area as measured along a center-to-center line 112b is relatively small for a given amount of poppet 42 displacement. As a result, very little flow is allowed through the valve 30, and the change in pressure of the gas on the inlet 38 side of the valve 30, or the proximal pressure, is very small for each incremental displacement of the poppet 42.

Further displacement of the poppet 42 to the right, or away from the valve seat 44, causes the valve 30 to open even more, as illustrated by position C of the poppet 42. When the poppet 42 is in position C, a center-to-center line 112c no longer passes through the poppet curved surface 110. This is due to the fact that the poppet curved surface 110 has a flat end 118 facing the valve seat 42 which is truncated in a plane which is normal to the linear axis of displacement of the poppet 42. The minimum cross-sectional area of the orifice now occurs along a line 113, drawn between the valve seat center of curvature 114 and the corner formed by the end 118 and the curved surface 110. As a result, the orifice area is abruptly increased, permitting high flow through the valve 30 and allowing the proximal gas to be quickly vented to the atmosphere. Once the valve 30 is open beyond the point at which the truncated end 118 of the poppet 42 increases the orifice area, small displacements of the poppet 42 result in larger changes in orifice area, which decreases the pressure drop through the valve 30. Consequently, the valve 30 can quickly open to a position at which little resistance to exhalation is encountered.

In a preferred embodiment, the radius of curvature of the valve seat curved surface 108 is 0.2 inches, and the radius of the curvature of the poppet curved surface 110 is 0.29 inches. The ratio of the valve seat curved surface 108 radius of curvature to the poppet curved surface 110 radius of curvature is thus approximately ⅔.

Figure 6:
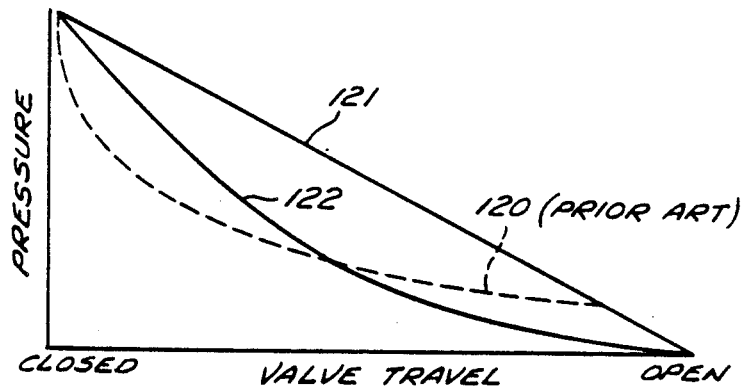
FIG. 6 is a graph of proximal pressure versus displacement of the valve member, with curves representing the performance of the present valve as well as a typical prior art valve.

A graph of pressure versus valve travel or poppet displacement in FIG. 6 illustrates the differences between the present poppet 42 and valve seat 44 design compared to prior art systems. For purposes of illustration, the curves drawn on the graph of FIG. 6 assume constant flow conditions. Curve 120 represents a prior art valve (not shown) where the mating surfaces of the poppet and valve seat are not curved. The rate of change in proximal pressure for a given amount of displacement of the poppet, or the "pressure gain", varies significantly over the range of poppet displacements, as indicated by the change slope of the curve 120. The problem associated with this variable pressure gain characteristic is the PEEP level is difficult to control as the valve closes since pressure gains increases as the valve approaches the closed position. Thus, small movements of the poppet results in large pressure changes. Further, it takes a long time before the valve is fully open to a position where there is low resistance to exhalation, due to the decrease in pressure gain once the valve is partially opened.

The straight line 121 represents the ideal or desired valve behavior, that is, constant pressure gain over all positions of the valve. The constant gain value, represented by the constant slope of the curve 121, is low enough to facilitate PEEP control as the valve closes, yet high enough for the valve to open quickly.

The performance of the present valve 30 is shown by curve 122. Although the present valve 30 does not exhibit constant gain characteristics, it represents a major improvement over the prior art in terms of approaching constant gain characteristics. As the poppet 42 approaches the closed position, the pressure gain increase is less than that in a conventional valve, such as that illustrated by the curve 120. The result is that the valve 30 can be closed very slowly, permitting accurate control over the PEEP level. This relatively low pressure gain region corresponds to the nearly closed position of the valve 30 where the center-to-center line 112 passes through both curved surfaces 108, 110 such as between positions A and B in FIG. 4.

As the valve 30 opens wider, the pressure gain decreases at a lesser rate than the conventional valve represented by curve 120, allowing the valve 30 to quickly assume a position in which there is low resistance to exhalation. This region of the curve 122 corresponds to the position of the valve 30 after the poppet 42 has passed the point where the truncated end 118 of the poppet affects the orifice area of the inlet 38, as illustrated by position C in FIG. 4.

Referring again to FIG. 3, the cam surface 54 has two distinct portions 124, 126 each having a different pitch or slope. The first portion 124 has a smaller pitch, and governs displacement of the stem 46 and poppet 42 as the poppet 42 approaches the closed position. Due to the small pitch of the cam surface first portion 124, a given number of steps of the stepper motor 48 and the resulting rotation of the cam 54 will cause little displacement of the stem 46 and poppet 42.

In contrast, the second portion 126 of the cam surface 54 has a steeper pitch, so that each step of the stepper motor 48 causes a larger amount of poppet 42 displacement. The second portion 126 governs motion of the poppet 42 after the valve 30 has been partially opened.

Figure 7:
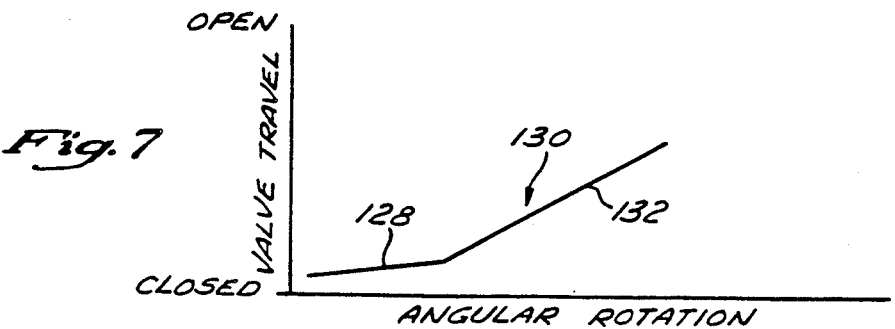
FIG. 7 is a graph of valve position versus cam rotation.

The graph of FIG. 7 illustrates how the valve position is affected by the pitch of the cam surface 54. Segment 128 of a curve 130 in FIG. 7 corresponds to the displacement of the poppet 42 caused by the cam surface first portion 124. As the poppet 42 approaches the closed position, a given amount of rotation of the cam 52 causes little change in the valve position enhancing the ability of the controller 26 to accurately control the PEEP level. Segment 132 of the curve 130 shows the valve behavior when the second portion 126 of the cam surface 54 is engaging the roller 56. Due to the steep pitch of the second portion 126, relatively little rotation of the cam 52 is required to cause the valve 30 to open wide enough to permit unobstructed venting of respiratory gases to the atmosphere.

Thus, the stepper motor 48 can directly drive the valve 30 without sacrificing control over PEEP, or the ability of valve 30 to open quickly to reduce resistance to exhalation.

What is claimed is:

1. An apparatus for use in a ventilator system having an exhaust which provides artificial respiration to a patient, said apparatus comprising:
   a stepper motor;
   a shaft coupled to said stepper motor, said shaft being movable by said stepper motor;
   a valve having means for coupling said valve to the exhaust of the ventilator system and means for connecting said valve to ambient air such that in a closed position no gas may flow through said valve from said means for coupling to said means for connecting and in a fully open position gas may flow through said valve from said means for coupling to said means for connecting;
   means coupled to said shaft for directly translating motion of said shaft into movement of said valve to change the flow of gas through said valve; and
   said valve includes means for providing a relatively low pressure gain when said valve is near its closed position and for providing a relatively high pressure gain when said valve is near its fully open position.

2. The apparatus of claim 1, wherein said valve further comprises:
   a valve seat located downstream from said coupling means and upstream from said connecting means having an orifice through which gases may flow; and
   a valve member which is movable relative to said valve seat to vary flow through said orifice, said means for translating motion of said valve into motion of said valve member causing motion of said valve member.

3. The apparatus of claim 2, wherein said valve member comprises a poppet and wherein said means for providing a relatively low pressure gain and a relatively high pressure gain comprises:
   a first convexly curved surface formed on said poppet said poppet which faces radially outward relative said orifice and forms the external periphery of said poppet, and;

a second convexly curved surface formed on said valve seat which faces radially inward relative said orifice and forms the internal periphery of said valve seat, wherein the radius of said first curved surface is greater than the radius of said second curved surface and said first curved surface and said second curved surface are shaped so as to sealingly engage when said valve is in said closed position.

4. The apparatus of claim 3, wherein said first convexly curved surface is truncated on the end of said poppet proximate said second convexly curved surface.

5. The apparatus of claim 2, wherein said translating means comprises a stem on which said valve member is removably mounted, and said valve further comprises a removable cap including a conduit having an inlet coupled to said coupling means, an outlet coupled to said connecting means and a removable diaphragm positioned between said cap and said stem forming a fluid-tight seal between said cap and said stem.

6. The apparatus of claim 2, wherein said translating means further comprises:
an elongate valve stem coupled to said shaft displaceable toward or away from said valve seat, said stem having an end proximate said valve seat;
a movable member mounted on said stem, said movable member being movable from a first position closer to said end of said stem proximate said valve seat to a second position further from said end of said stem proximate said valve seat along said stem; and
means for biasing said movable member toward said first position, said valve member being mounted on said movable member such that upon engagement of said valve seat by said valve member, displacement of said stem toward said valve seat moves said movable member toward said second position.

7. The apparatus of claim 1, wherein said translating means includes means for providing a relatively low pressure gain when said valve is near its closed position and for providing a relatively high pressure gain when said valve is near its fully open position.

8. The apparatus of claim 7, wherein said translating means comprises:
a cam mounted on said shaft;
a cam follower which engages a surface on said cam, said cam surface being pitched to cause displacement of said cam follower upon rotation of said cam; and
a stem, one end of said stem being secured to said cam follower, the other end of said stem being secured to said valve member so that displacement of said stem causes displacement of said valve member relative to said valve seat;
and wherein said means for providing a relatively low and a relatively high pressure gain comprises:
a first portion on said cam surface which has a small pitch so that for a given amount of cam rotation, a small displacement of said valve member results, said cam follower engaging said first portion when said valve is closed and proximate the closed position; and
a second portion on said cam surface which has a larger pitch so that for a given amount of cam rotation, a large displacement of said valve member results, said cam follower engaging said second portion when said valve is substantially open and proximate the fully open position.

9. The apparatus of claim 1, wherein said valve defines a first valve body and a second valve body movable with respect to one another and located downstream from said coupling means and upstream from said connecting means, wherein said means for providing a relatively low pressure gain and a relatively high pressure gain comprises:
a first convexly curved surface formed on said first valve body; and
a second convexly curved surface formed on said second valve body, said first body having an end facing said second body and said second body having an end facing said first body, wherein said first surface faces radially outward relative said second body facing end of said first body and forms an external periphery of said first valve body and said second surface faces radially inward relative to said first body facing end of said second body and forms an inner periphery of said second valve body, wherein the radius of said first curved surface is greater than the radius of said second curved surface.

10. An apparatus for use in a ventilator having an exhaust which provides artificial respiration to a patient, said apparatus comprising:
a stepper motor;
a shaft coupled to said stepper motor, said shaft being movable by said stepper motor;
a valve having means for coupling said valve to the exhaust of the ventilator system and means for connecting said valve to ambient air such that in a closed position no gas may flow through said valve from said means for coupling to said means for connecting and in a fully open position gas may flow through said valve from said means for coupling to said means for connecting;
means coupled to said shaft for directly translating motion of said shaft into movement of said valve to change the flow of gas through said valve; and
said translating means includes means for providing a relatively low pressure gain when said valve is near its closed position and for providing a relatively high pressure gain when said valve is near its fully open position.

11. The apparatus of claim 10, wherein said valve further comprises:
a valve seat located downstream from said coupling means and upstream from said connecting means having an orifice through which gases may flow; and
a valve member which is movable relative to said valve seat to vary flow through said orifice, said means for translating motion of said valve into motion of said valve member causing motion of said valve member.

12. The apparatus of claim 11, wherein said translating means comprises:
a cam mounted on said shaft;
a cam follower which engages a surface on said cam, said cam surface being pitched to cause displacement of said cam follower upon rotation of said cam; and
a stem, one end of said stem being secured to said cam follower, the other end of said stem being secured to said valve member so that displacement of said stem causes displacement of said valve member relative to said valve seat;

and wherein said means for providing a relatively low and a relatively high pressure gain comprises:
- a first portion on said cam surface which has a small pitch so that for a given amount of cam rotation, a small displacement of said valve member results, said cam follower engaging said first portion when said valve is closed and proximate the closed position; and
- a second portion on said cam surface which has a larger pitch so that for a given amount of cam rotation, a large displacement of said valve member results, said cam follower engaging said second portion when said valve is substantially open and proximate the fully open position.

13. The apparatus of claim 11, wherein said translating means comprises a stem on which said valve member is removably mounted, and said valve further comprises a removable cap including a conduit having an inlet coupled to said coupling means, an outlet coupled to said connecting means and a removable diaphragm positioned between said cap and said stem forming a fluid-tight seal between said cap and said stem.

14. The apparatus of claim 11, wherein said translating means further comprises:
- an elongate valve stem coupled to said shaft displaceable toward or away from said valve seat, said stem having an end proximate said valve seat;
- a movable member mounted on said stem, said movable member being movable from a first position closer to said end of said stem proximate said valve seat to a second position further from said end of said stem proximate said valve seat along said stem; and
- means for biasing said movable member toward said first position, said valve member being mounted on said movable member such that upon engagement of said valve seat by said valve member, displacement of said stem toward said valve seat moves said movable member toward said second position.

* * * * *